United States Patent
Osafune et al.

(10) Patent No.: US 9,890,357 B2
(45) Date of Patent: Feb. 13, 2018

(54) METHOD FOR INDUCING DIFFERENTIATION OF HUMAN PLURIPOTENT STEM CELLS INTO INTERMEDIATE MESODERM CELLS

(71) Applicant: Kyoto University, Kyoto-shi (JP)

(72) Inventors: Kenji Osafune, Kyoto (JP); Toshikazu Araoka, Kyoto (JP)

(73) Assignee: KYOTO UNIVERSITY, Kyoto-shi (JP)

(*) Notice: Subject to any disclaimer, the term of this patent is extended or adjusted under 35 U.S.C. 154(b) by 0 days.

(21) Appl. No.: 14/366,169

(22) PCT Filed: Dec. 19, 2012

(86) PCT No.: PCT/JP2012/083762
§ 371 (c)(1),
(2) Date: Jun. 17, 2014

(87) PCT Pub. No.: WO2013/094771
PCT Pub. Date: Jun. 27, 2013

(65) Prior Publication Data
US 2014/0363888 A1    Dec. 11, 2014

Related U.S. Application Data

(60) Provisional application No. 61/577,345, filed on Dec. 19, 2011.

(51) Int. Cl.
| | | |
|---|---|---|
| *A61K 35/22* | (2015.01) | |
| *C12N 5/071* | (2010.01) | |
| *C12N 5/0735* | (2010.01) | |
| *C12N 5/073* | (2010.01) | |

(52) U.S. Cl.
CPC ......... *C12N 5/0605* (2013.01); *C12N 5/0686* (2013.01); *C12N 2501/155* (2013.01); *C12N 2501/385* (2013.01); *C12N 2501/415* (2013.01); *C12N 2501/727* (2013.01); *C12N 2501/999* (2013.01); *C12N 2506/45* (2013.01)

(58) Field of Classification Search
None
See application file for complete search history.

(56) References Cited

U.S. PATENT DOCUMENTS

| | | | |
|---|---|---|---|
| 5,843,780 A | | 12/1998 | Thomson |
| 2013/0189780 A1 | * | 7/2013 | Shoemaker et al. .......... 435/375 |
| 2016/0137985 A1 | * | 5/2016 | Osafune ............... A61K 35/545 424/93.7 |

FOREIGN PATENT DOCUMENTS

| | | |
|---|---|---|
| WO | 2007 069666 | 6/2007 |
| WO | 2012 011610 | 1/2012 |

OTHER PUBLICATIONS

Araoka et al, Efficient and Rapid Induction of Human iPSCs/ESCs into Nephrogenic Intermediate Mesoderm Using Small Molecule-Based Differentiation Methods, PLOS ONE, 2014, vol. 9(1), pp. 1-14.*

* cited by examiner

*Primary Examiner* — Maria Marvich
(74) *Attorney, Agent, or Firm* — Oblon, McClelland, Maier & Neustadt, L.L.P.

(57) ABSTRACT

The present invention provides a method for inducing differentiation of a human pluripotent stem cell into an intermediate mesoderm cell without the use of a growth factor. Such method comprises performing culture in a medium containing a specific compound, so as to induce differentiation of a human pluripotent stem cell into an intermediate mesoderm cell.

20 Claims, 9 Drawing Sheets

Differentiation time

PC: Positive control
(human adult kidney & human adult testis)

Bars; 100 μm

Bars; 100 μm

METHOD FOR INDUCING DIFFERENTIATION OF HUMAN PLURIPOTENT STEM CELLS INTO INTERMEDIATE MESODERM CELLS

TECHNICAL FIELD

The present invention relates to a method for inducing differentiation of a pluripotent stem cell into an intermediate mesoderm cell. The present invention also relates to a method for producing a metanephric cell from the intermediate mesoderm cell thus obtained.

BACKGROUND ART

The kidney is an important organ that functions to maintain physical health by removing, by filtration, waste products, such as harmful or detrimental substances generated as a result of metabolic activity within a living organism, from the blood.

An example of a kidney disorder is kidney failure, and an example of a therapeutic method therefor is artificial dialysis. However, the burden imposed by medical expenses required for such therapeutic method is high, and thus the kidney failure is still a world-wide problem, not only from medical perspective, but also from medical economic aspect. Another example of a therapeutic method for kidney failure is renal transplantation, although shortage of donor organs is a serious issue of concern.

Meanwhile, pluripotent cells such as embryonic stem cells (ES cells) and induced pluripotent stem cells (iPS cells), which can be obtained via introduction of undifferentiated cell-specific genes into somatic cells, have been reported (U.S. Pat. No. 5,843,780 and WO 2007/069666). As a therapeutic method for kidney failure, therefore, a therapeutic method that involves transplanting renal cells obtained by inducting differentiation of these pluripotent stem cells has been investigated. Moreover, development of therapeutic agents using homogeneous renal cells from these pluripotent stem cells is also under consideration.

The mammalian kidney is formed through three stages of development of the pronephros, the mesonephros, and the metanephros. Among these stages, the metanephros is known to be generated in the posterior region of the intermediate mesoderm. In this context, a method for inducing differentiation of mouse pluripotent stem cells into the intermediate mesoderm for nephrogenesis has been investigated (Mae, S. et al., 2010, Biochem. Biophys. Res. Commun., 393: 877-882). In addition, human pluripotent stem cells are successfully induced to differentiate into the intermediate mesoderm cells with the use of Activin A, Wnt, and BMP (International Application No. PCT/JP2011/067181 (WO 2012/011610)). Although such methods involving the use of growth factors are disadvantageous in terms of their very high cost, to date, no methods for inducing differentiation of human pluripotent stem cells into intermediate mesoderm cells without the use of growth factors have been reported.

DISCLOSURE OF THE INVENTION

Problem to be Solved by the Invention

Under the above circumstances, it is an object of the present invention to provide a method for inducing differentiation of a human pluripotent stem cell into an intermediate mesoderm cell without the use of a growth factor. More particularly, it is the object of the present invention to provide a method for inducing differentiation of a human pluripotent stem cell into an intermediate mesoderm cell via substitution of a growth factor with a specific compound.

Means for Solving the Problem

The present inventors have conducted concentrated studies in order to attain the above objects. As a result, they have found that a human pluripotent stem cell can be induced to differentiate into an intermediate mesoderm cell by performing culture in a medium containing a specific compound. This has led to the completion of the present invention.

Specifically, the present invention includes the following.
(1) A method for producing an intermediate mesoderm cell from a human pluripotent stem cell comprising the following steps of:
(i) culturing a human pluripotent stem cell in a medium containing a GSK-3 beta inhibitor or a GSK-3 beta inhibitor and a retinoic acid derivative; and
(ii) culturing the cell obtained in the step (i) in a medium containing a retinoic acid derivative.
(2) The method according to (1), wherein the GSK-3 beta inhibitor is CHIR99021.
(3) The method according to (1) or (2), wherein the retinoic acid derivative is AM580 or TTNPB.
(4) The method according to any one of (1) to (3), wherein the human pluripotent stem cell is a human iPS cell or human ES cell.
(5) The method according to any one of (1) to (4), wherein the intermediate mesoderm cell is an OSR1-positive cell.
(6) The method according to any one of (1) to (5), wherein step (i) comprises dissociating the human pluripotent stem cells into single cells.
(7) The method according to (6), wherein the medium used in step (i) further comprises a ROCK inhibitor.
(8) The method according to (7), wherein the ROCK inhibitor is Y-27632.
(9) The method according to any one of (1) to (8), wherein the culture period of step (i) is up to 2 days and that of step (ii) is at least 3 days.
(10) The method according to (9), wherein the culture period of step (i) is 2 days and that of step (ii) is 8 days.
(11) A kit for producing an intermediate mesoderm cell from a human pluripotent stem cell comprising a GSK-3 beta inhibitor and a retinoic acid derivative.
(12) The kit according to (11), wherein the GSK-3 beta inhibitor is CHIR99021.
(13) The kit according to (11) or (12), wherein the retinoic acid derivative is AM580 or TTNPB.
(14) The kit according to any one of (11) to (13), which further comprises a cell dissociation reagent for human pluripotent stem cells.
(15) The kit according to any one of (11) to (14), which further comprises a ROCK inhibitor.
(16) The kit according to (15), wherein the ROCK inhibitor is Y-27632.
(17) A method for producing metanephric cell comprising inducing differentiation of a human pluripotent stem cell into an intermediate mesoderm cell by the method according to any one of (1) to (10).
(18) The method according to (17), wherein the metanephric cell is selected from the group consisting of metanephric mesenchyme cell, metanephric stroma cell, ureteric bud cell podocyte and proximal tubule cell.

(19) The method according to (17) or (18), further comprising the step of culturing the intermediate mesoderm cell in the medium containing Wnt3a and BMP7.
(20) A method for producing luminal structure constructed with renal tubule cells comprising the step of forming sphere consisting of an intermediate mesoderm cell produced by the method according to any one of (1) to (10).
(21) A method for producing luminal structure constructed with renal tubule cells comprising the step of culturing an intermediate mesoderm cell with metanephric cell, wherein the intermediate mesoderm cell is produced by the method according to any one of (1) to (10).
(22) The method according to (21), wherein the metanephric cell is obtained from E11.5 mouse embryos.

This Application claims benefit of U.S. Provisional Patent Application No. 61/577,345, filed Dec. 19, 2011, which is incorporated by reference in its entirety herein.

Effects of the Invention

According to the method of the present invention, a human pluripotent stem cell can be induced to differentiate into an intermediate mesoderm cell without the use of a growth factor. In addition, the present invention has the effects described below.
1. The induction method is simple and involves little complications.
2. A retinoic acid derivative, such as AM580 or TTNPB, is considered to activate an intranuclear receptor of retinoic acid (RAR) and exert its effects through a retinoic acid pathway. Since activity of the compound is higher than that of all-trans retinoic acid (ATRA) having similar effects, it can exert its effects at low concentrations.
3. Because of its lower cytotoxicity compared with ATRA, use of a retinoic acid derivative, such as AM580 or TTNPB, at high concentrations results in more effective induction of differentiation into intermediate mesoderm cells.
4. There are 3 RAR subtypes (i.e., alpha, beta, and gamma), and a retinoic acid derivative, such as AM580 or TTNPB, is capable of selectively activating an RAR subtype associated with differentiation into intermediate mesoderm cells. Accordingly, side effects can be prevented by eliminating unnecessary signals.
5. The novel induction method 3 described in the Examples below can shorten the number of days necessary for inducing differentiation.

EMBODIMENTS FOR CARRYING OUT THE INVENTION

Figure 1:
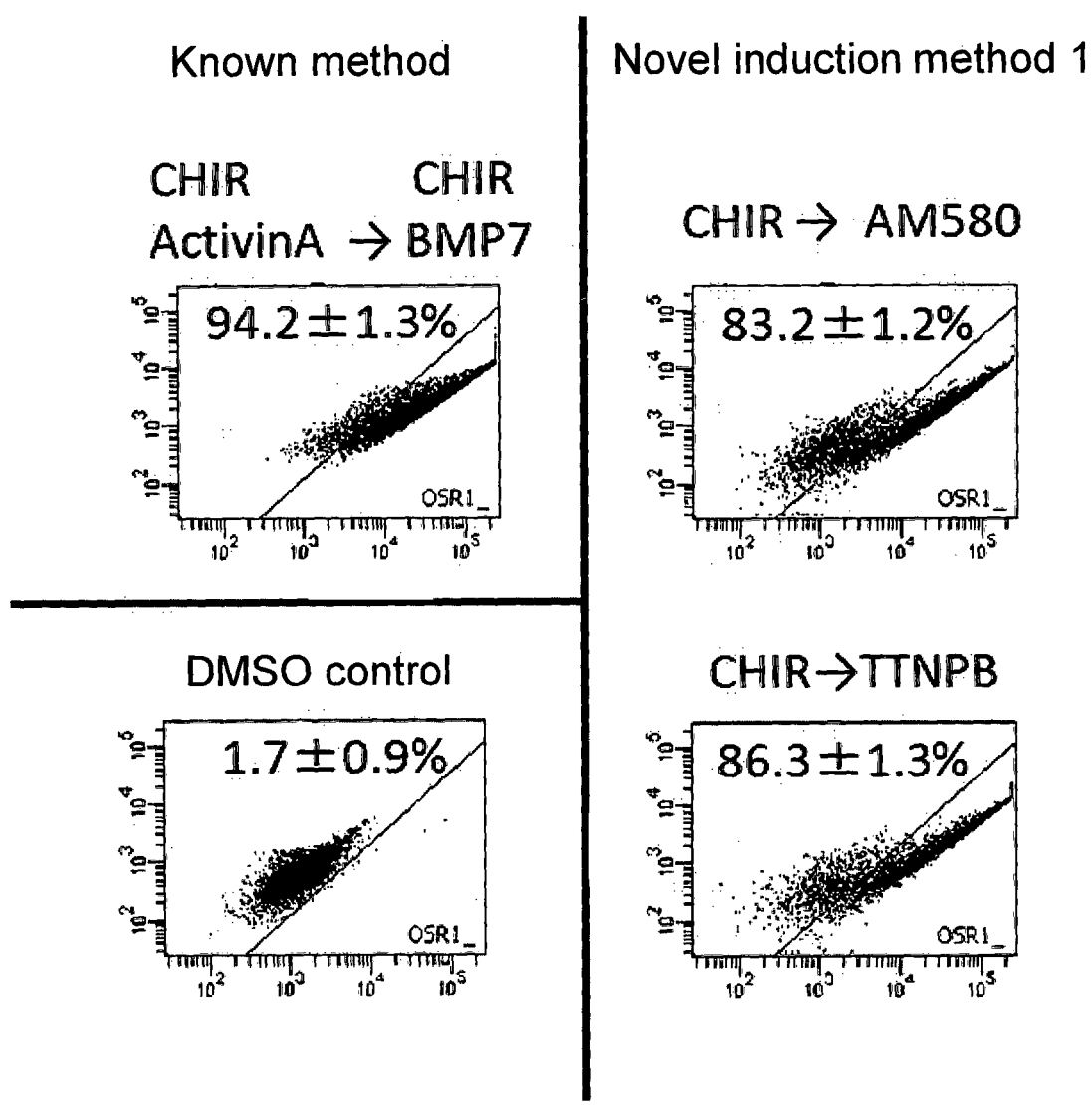
FIG. 1 shows the results of flow cytometric analysis of the cells obtained by inducing differentiation of the iPS cells on day 11 by the following methods using OSR1 (GFP) expression as the indicator: a method in which a medium containing CHIR99021 (indicated as "CHIR" in FIGS. 1 to 3) and Activin A is exchanged with a medium containing CHIR99021 and BMP7 (known method, upper left); a control method in which a medium supplemented with DMSO is used (DMSO control, lower left); and a method in which a medium containing CHIR99021 is exchanged with a medium containing AM580 (upper right) or TTNPB (lower right) (novel induction method 1). Numerals in the figure indicate percentages of OSR1-positive cells.

Hereafter, the present invention is described in detail.
The present invention relates to a method for inducing differentiation of a pluripotent stem cell into an intermediate mesoderm cell. The present invention also relates to a method for producing a metanephric cell from the intermediate mesoderm cell thus obtained.
<Pluripotent Stem Cells>
Pluripotent stem cells that can be used in the present invention are stem cells having both pluripotency, by which the cells are capable of differentiating into all cells existing in the living body, and proliferation potency. Examples of these pluripotent stem cells include, but are not limited to, embryonic stem cells (ES cells), embryonic stem cells from clone embryos obtained by nuclear transplantation (ntES cells), germline stem cells ("GS cells"), embryonic germ cells ("EG cells"), and induced pluripotent stem (iPS) cells.

Examples of preferable pluripotent stem cells include ES cells, ntES cells, and iPS cells.

(A) Embryonic Stem Cells

ES cells are stem cells having pluripotency and an ability to proliferate by self-replication, which are established from the inner cell mass of early embryos (e.g., blastocysts) of a mammal, such as a human, or a mouse.

ES cells are embryo-derived stem cells derived from the inner cell mass of blastocysts that are embryos at 8-cell stage or morula stage of fertilized eggs. ES cells have so-called pluripotency, which is the ability to differentiate into all cells for forming a matured body, and an ability to proliferate by self-replication. The ES cells were first discovered in mice in 1981 (M. J. Evans and M. H. Kaufman, 1981, Nature 292: 154-156). Thereafter, ES cell lines were established in primates including humans, monkeys, and the like (J. A. Thomson et al., 1998, Science 282: 1145-1147; J. A. Thomson et al., 1995, Proc. Natl. Acad. Sci., U.S.A., 92: 7844-7848; J. A. Thomson et al., 1996, Biol. Reprod., 55: 254-259; and J. A. Thomson and V. S. Marshall, 1998, Curr. Top. Dev. Biol., 38: 133-165).

ES cells can be established by removing the inner cell mass from blastocysts of fertilized eggs of a subject animal and then culturing the inner cell mass on a fibroblast feeder. Also, the maintenance of ES cells by subculture can be carried out using a medium supplemented with substances such as leukemia inhibitory factors (LIF) and basic fibroblast growth factors (bFGF). Methods for establishing and maintaining human and monkey ES cells are described in, for example, H. Suemori et al., 2006, Biochem. Biophys. Res. Commun., 345: 926-932; M. Ueno et al., 2006, Proc. Natl. Acad. Sci., U.S.A., 103: 9554-9559; H. Suemori et al., 2001, Dev. Dyn., 222: 273-279; and H. Kawasaki et al., 2002, Proc. Natl. Acad. Sci., U.S.A., 99: 1580-1585.

An example of a medium that can be used for preparation of ES cells is a DMEM/F-12 medium supplemented with 0.1 mM 2-mercaptoethanol, 0.1 mM nonessential amino acids, 2 mM L-glutamic acid, 20% KSR, and 4 ng/ml bFGF. Human ES cells can be maintained under a wet atmosphere of 5% $CO_2$ at 37 degrees C. Also, it is necessary that ES cell subculture be carried out every 3 or 4 days. At this time, the subculture can be carried out by using 0.25% trypsin and 0.1 mg/ml collagenase IV in PBS containing 1 mM $CaCl_2$ and 20% KSR, for example.

ES cells can generally be selected using the expression of gene markers, such as alkaline phosphatase, Oct-3/4, or Nanog, as indicators. In particular, human ES cells can be selected by detecting the expression of gene markers such as OCT-3/4 and NANOG by Real-Time PCR and/or by detecting the cell surface antigens, i.e., SSEA-3, SSEA-4, TRA-1-60, and TRA-1-81, by immunostaining (Klimanskaya I. et al., 2006, Nature, 444: 481-485).

Human ES cell lines, such as KhES-1, KhES-2, and KhES-3, are available from the Institute for Frontier Medical Sciences, Kyoto University (Kyoto, Japan).

(B) Germline Stem Cells

Germline stem cells are testis-derived pluripotent stem cells that serve as origins for spermatogenesis. The germline stem cells can also be induced so as to differentiate into a variety of cell lines in a manner similar to that possible with ES cells. For example, the germline stem cells have properties such that a chimeric mouse can be produced when they are transplanted into the mouse blastocyst (M. Kanatsu-Shinohara et al., 2003, Biol. Reprod., 69: 612-616; K. Shinohara et al., 2004, Cell, 119: 1001-1012). The germline stem cells are self-replicable in a medium containing a glial cell line-derived neurotrophic factor (GDNF), and the germline stem cells can be obtained by repeating subculture of cells under culture conditions similar to those for ES cells (Masanori Takebayashi et al., 2008, Experimental Medicine, Vol. 26, No. 5 (Extra Number), pp. 41-46, YODOSHA (Tokyo, Japan)).

(C) Embryonic Germ Cells

Embryonic germ cells are established from primordial germ cells in the prenatal period and have pluripotency similar to that of ES cells. Embryonic germ cells can be established by culturing primordial germ cells in the presence of substances such as LIF, bFGF, or stem cell factors (Y. Matsui et al., 1992, Cell, 70: 841-847; J. L. Resnick et al., 1992, Nature, 359: 550-551).

(D) Induced Pluripotent Stem Cells

Induced pluripotent stem (iPS) cells can be prepared by introducing specific nuclear reprogramming substances in the form of DNAs or proteins into somatic cells or by increasing the expression levels of the endogenous mRNAs and proteins of the nuclear reprogramming substances with the use of an agent. The iPS cells are somatic cell-derived artificial stem cells having properties almost equivalent to those of ES cells, such as pluripotency and the ability to proliferate by self-replication (K. Takahashi and S. Yamanaka, 2006, Cell, 126: 663-676; K. Takahashi et al., 2007, Cell, 131: 861-872; J. Yu et al., 2007, Science, 318: 1917-1920; M. Nakagawa et al., 2008, Nat. Biotechnol., 26: 101-106; International Publication WO 2007/069666; and International Publication WO 2010/068955). The nuclear reprogramming substances may be genes specifically expressed in ES cells, genes playing an important role in maintenance of undifferentiation of ES cells, or gene products thereof. Examples of the nuclear reprogramming substances include, but are not particularly limited to, Oct3/4, Klf4, Klf1, Klf2, Klf5, Sox2, Sox1, Sox3, Sox15, Sox17, Sox18, c-Myc, L-Myc, N-Myc, TERT, SV40 Large T antigen, HPV16 E6, HPV16 E7, Bmi1, Lin28, Lin28b, Nanog, Esrrb, Esrrg, and Glis1. These reprogramming substances may be used in combination upon establishment of iPS cells. Such combinations may contain at least one, two, or three reprogramming substances above and preferably contain four reprogramming substances above.

The nucleotide sequence information of the mouse or human cDNA of each of the above nuclear reprogramming substances and the amino acid sequence information of a protein encoded by the cDNA can be obtained from the NCBI database with reference to the NCBI accession numbers provided in WO 2007/069666. Also, the mouse and human cDNA and amino acid sequence information of L-Myc, Lin28, Lin28b, Esrrb, Esrrg and Glis1 can each be obtained from the NCBI database with reference to the NCBI accession numbers listed in Table 1. Persons skilled in the art can prepare desired nuclear reprogramming substances by known methods based on the cDNA or amino acid sequence information.

TABLE 1

| Genes | Mice | Humans |
| --- | --- | --- |
| L-Myc | NM_008506 | NM_001033081 |
| Lin28 | NM_145833 | NM_024674 |
| Lin28b | NM_001031772 | NM_001004317 |
| Esrrb | NM_011934 | NM_004452 |
| Esrrg | NM_011935 | NM_001438 |
| Glis1 | NM_147221 | NM_147193 |

These nuclear reprogramming substances may be introduced in the form of proteins into somatic cells by means of, for example, lipofection, binding with a cell membrane-permeable peptide, or microinjection. Alternatively, they can also be introduced in the form of DNA into somatic cells by means of, for example, a virus, plasmid, or artificial chromosome vector, lipofection, a liposome, or microinjection. Examples of virus vectors include a retrovirus vector, a lentivirus vector (Cell, 126, pp. 663-676, 2006; Cell, 131, pp. 861-872, 2007; Science, 318, pp. 1917-1920, 2007), an adenovirus vector (Science, 322, 945-949, 2008), an adeno-associated virus vector, and a Sendai virus vector (Proc. Jpn. Acad. Ser. B. Phys. Biol. Sci., 85, 348-62, 2009). Also, examples of artificial chromosome vectors include a human artificial chromosome (HAC), a yeast artificial chromosome (YAC), and a bacterial artificial chromosome (BAC/PAC). Plasmids for mammalian cells can be used (Science, 322: 949-953, 2008). The vectors can contain regulatory sequences such as a promoter, an enhancer, a ribosome binding sequence, a terminator, and a polyadenylation site, so that a nuclear reprogramming substance can be expressed. Examples of the promoter usable herein include an EF1 alpha promoter, a CAG promoter, an SR alpha promoter, an SV40 promoter, an LTR promoter, a CMV (cytomegalovirus) promoter, an RSV (Rous sarcoma virus) promoter, MoMuLV (Moloney murine leukemia virus) LTR, and an HSV-TK (herpes simplex virus thymidine kinase) promoter. Examples of particularly preferable promoters include an EF1 alpha promoter, a CAG promoter, MoMuLV LTR, a CMV promoter, and an SR alpha promoter. The vectors may further contain, if necessary, a selection marker sequence, such as a drug resistance gene (e.g., a kanamycin resistance gene, an ampicillin resistance gene, or a puromycin resistance gene), a thymidine kinase gene, and a diphtheria toxin gene, and a reporter gene sequence, such as a green fluorescent protein (GFP), beta glucuronidase (GUS), or FLAG. After the vector is introduced into somatic cells, a gene encoding a nuclear reprogramming substance or a gene encoding a nuclear reprogramming substance linked to a promoter is cleaved. To this end, the vector may have LoxP sequences located before and after the relevant portion. In another preferable embodiment, a method that involves incorporating a transgene into the chromosome using a transposon, causing a transferase to act on cells using a plasmid or adenovirus vector, and then completely removing the transgene from the chromosome can be used. An example of a preferable transposon is piggyBac, which is a lepidopteran insect-derived transposon (Kaji, K. et al., Nature, 458: 771-775, 2009; Woltjen et al., Nature, 458: 766-770, 2009; WO 2010/012077). Furthermore, the vectors may also comprise sequences of replication origins for lymphotrophic herpes virus, BK virus, and Bovine papilloma virus and sequences involved in the replication, so that the sequences can be replicated without incorporation into the chromosome so as to be present episomally. For example, EBNA-1 and oriP sequences, or Large T and SV40ori sequences may be included in the vectors (WO 2009/115295, WO 2009/157201, and WO 2009/149233). In order to simultaneously introduce two or more nuclear reprogramming substances, an expression vector that enables polycistronic expression may be used. For polycistronic expression, the sequences of IRES or a foot and mouth disease virus (FMDV) 2A coding region may be linked between the gene-coding sequences (Science, 322: 949-953, 2008, WO 2009/092042, and WO 2009/152529).

Upon nuclear reprogramming, for example, histone deacetylase (HDAC) inhibitors [e.g., low-molecular-weight inhibitors, such as valproic acid (VPA) (Nat. Biotechnol., 26(7): 795-797, 2008), trichostatin A, sodium butyrate, MC 1293, and M344, and nucleic acid expression inhibitors, such as siRNA and shRNA against HDAC (e.g., HDAC1 siRNA Smartpool™, Millipore, and HuSH 29mer shRNA constructs against HDAC1, OriGene)], DNA methyltransferase inhibitors (e.g., 5'-azacytidine) (Nat. Biotechnol., 26(7): 795-797, 2008), G9a histone methyltransferase inhibitors [e.g., low-molecular-weight inhibitors, such as BIX-01294 (Cell Stem Cell, 2: 525-528, 2008), and nucleic acid expression inhibitors, such as siRNA and shRNA against G9a (e.g., G9a siRNA (human), Santa Cruz Biotechnology)], L-channel calcium agonists (e.g., Bayk8644) (Cell Stem Cell, 3, 568-574, 2008), p53 inhibitors (e.g., siRNA and shRNA against p53) (Cell Stem Cell, 3, 475-479, 2008), Wnt Signaling Activator (e.g., soluble Wnt3a) (Cell Stem Cell, 3, 132-135, 2008), growth factors such as LIF or bFGF, ALK5 inhibitors (e.g., SB431542) (Nat. Methods, 6: 805-8, 2009), mitogen-activated protein kinase signaling inhibitors, glycogen synthase kinase-3 inhibitors (PloS Biology, 6(10), 2237-2247, 2008), or miRNA such as miR-291-3p, miR-294, or miR-295 (R. L., Judson et al., Nat. Biotech., 27: 459-461, 2009) can be used, in addition to the above-described factors. Thus, the efficiency for inducing iPS cells can be improved.

Examples of agents used in the method for increasing the expression level of the endogenous protein of a nuclear reprogramming substance include 6-bromoindirubin-3'-oxime, indirubin-5-nitro-3'-oxime, valproic acid, 2-(3-(6-methylpyridin-2-yl)-1H-pyrazol-4-yl)-1,5-naphthyridine, 1-(4-methylphenyl)-2-(4,5,6,7-tetrahydro-2-imino-3(2H)-benzothiazolyl)ethanone HBr (pifithrin-alpha), prostaglandin J2, and prostaglandin E2 (WO 2010/068955).

Examples of a culture medium for inducing iPS cells include: (1) a DMEM, DMEM/F12, or DME medium containing 10% to 15% FBS (wherein these media may further optionally contain LIF, penicillin/streptomycin, puromycin, L-glutamine, nonessential amino acids, beta-mercaptoethanol, and the like); and, (2) a medium for ES cell culture containing bFGF or SCF, such as a medium for mouse ES cell culture (e.g., TX-WES medium, Thromb-X) and a medium for primate ES cell culture (e.g., a medium for primate (human & monkey) ES cells, ReproCELL, Kyoto, Japan, mTeSR-1).

Examples of culture methods are as follows. Somatic cells are brought into contact with nuclear reprogramming substances (DNAs or proteins) on a DMEM or DMEM/F12 medium containing 10% FBS at 37 degrees C. in the presence of 5% $CO_2$, and the cells are cultured for about 4 to 7 days. Subsequently, the cells are reseeded on feeder cells (e.g., mitomycin C-treated STO cells or SNL cells). About 10 days after contact of somatic cells with nuclear reprogramming substances, the cells are cultured on a bFGF-containing medium for primate ES cell culture. About 30 to 45 or more days after the contact, ES cell-like colonies can be formed. The resulting cells may also be cultured under conditions in which the oxygen concentration is as low as 5% to 10% in order to increase the efficiency for inducing iPS cells.

Alternatively, cells may be cultured on a DMEM medium containing 10% FBS (which may further optionally contain LIF, penicillin/streptomycin, puromycin, L-glutamine, nonessential amino acids, beta-mercaptoethanol, and the like) on feeder cells (e.g., mitomycin C-treated STO cells or SNL cells). About 25 to 30 or more days later, ES cell-like colonies can be formed.

During the above culture, the medium is exchanged with fresh medium once a day from day 2 after the initiation of culture. In addition, the number of somatic cells used for nuclear reprogramming is not limited, but it ranges from approximately 5×10³ cells to approximately 5×10⁶ cells per 100-cm² area of a culture dish.

When genes including a drug resistance gene are used as a marker gene, cells expressing the marker gene can be selected by conducting culture in a medium containing a relevant drug (i.e., a selective medium). Also, cells expressing the marker gene can be detected via observation under a fluorescence microscope when the marker gene is a fluorescent protein-encoding gene, via addition of a luminescent substrate when the marker gene is a luminescent enzyme-encoding gene, or via addition of a chromogenic substrate when the marker gene is a chromogenic enzyme-encoding gene.

The term "somatic cell" used herein may refer to any cell other than germ cells from mammals (e.g., humans, mice, monkeys, pigs, and rats). Examples thereof include keratinizing epithelial cells (e.g., keratinizing epidermal cells), mucosal epithelial cells (e.g., epithelial cells of the tongue surface layer), exocrine epithelial cells (e.g., mammary glandular cells), hormone-secreting cells (e.g., adrenal medullary cells), cells for metabolism and storage (e.g., hepatocytes), boundary-forming luminal epithelial cells (e.g., type I alveolar cells), luminal epithelial cells of internal tubules (e.g., vascular endothelial cells), ciliated cells having a carrying capacity (e.g., airway epithelial cells), cells for secretion to an extracellular matrix (e.g., fibroblasts), contractile cells (e.g., smooth muscle cells), cells of the blood and the immune system (e.g., T lymphocytes), cells involved in sensation (e.g., rod cells), autonomic nervous system neurons (e.g., cholinergic neurons), sense organ and peripheral neuron supporting cells (e.g., satellite cells), nerve cells and glial cells of the central nervous system (e.g., astroglial cells), chromocytes (e.g., retinal pigment epithelial cells), and progenitor cells thereof (tissue progenitor cells). Without particular limitation concerning the degree of cell differentiation, the age of an animal from which cells are collected, or the like, both undifferentiated progenitor cells (also including somatic stem cells) and terminally-differentiated mature cells can be similarly used as origins for somatic cells in the present invention. Examples of undifferentiated progenitor cells include tissue stem cells (somatic stem cells) such as neural stem cells, hematopoietic stem cells, mesenchymal stem cells, and dental pulp stem cells.

In the present invention, mammals from which somatic cells are collected are not particularly limited and are preferably humans.

(E) Clone Embryo-derived ES Cells Obtained by Nuclear Transplantation ntES cells are clone embryo-derived ES cells prepared by nuclear transplantation techniques having properties almost the same as those of fertilized egg-derived ES cells (T. Wakayama et al., 2001, Science, 292: 740-743; S. Wakayama et al., 2005, Biol. Reprod., 72: 932-936; J. Byrne et al., 2007, Nature, 450: 497-502). Specifically, ntES (nuclear transfer ES) cells are ES cells which are established from the inner cell mass of blastocysts from a clone embryo that is obtained via substitution of the nucleus of an unfertilized egg with the nucleus of a somatic cell. For preparation of ntES cells, nuclear transplantation techniques (J. B. Cibelli et al., 1998, Nat. Biotechnol., 16: 642-646) and the above ES cell preparation techniques are used in combination (Kiyoka Wakayama et al., 2008, Experimental Medicine, Vol. 26, No. 5 (Extra Number), pp. 47-52). Upon nuclear transplantation, the nucleus of a somatic cell is injected into a mammalian enucleated unfertilized egg, and the resultant cell is subsequently cultured for several hours, so that the reprogramming can be carried out.

(F) Fusion Stem Cells

Fusion stem cells are prepared by fusing somatic cells to eggs or ES cells, and thus they have pluripotency similar to that of the ES cells to be fused thereto. Moreover, the fusion stem cells also have genes peculiar to somatic cells (Tada, M. et al., Curr. Biol. 11: 1553-8, 2001; Cowan, C. A. et al., Science, 2005, Aug. 26, 309 (5739): 1369-73).

<Method for Inducing Differentiation of Pluripotent Stem Cells into Intermediate Mesoderm Cells>

According to the present invention, a method comprising the following steps can be used to induce differentiation of pluripotent stem cells, such as ES cells or iPS cells, into intermediate mesoderm cells:

(i) a step of culturing pluripotent stem cells, such as human pluripotent stem cells, in a medium containing a glycogen synthase kinase 3 beta (GSK-3 beta) inhibitor or a GSK-3 beta inhibitor and a retinoic acid derivative (first step); and (ii) a subsequent step of culturing the cells obtained after the step (1) in a medium containing a retinoic acid derivative (second step).

The term "intermediate mesoderm cell" used herein refers to a cell capable of differentiating into pronephros, mesonephros, mesonephric duct, metanephros, adrenal cortex, or genital gland, and it preferably refers to a cell expressing OSR1 (odd-skipped related 1); i.e., an OSR1-positive cell.

In the present invention, intermediate mesoderm cells obtained via induced differentiation may be provided as a cell population containing other cell species or as a purified cell population.

From an ethical standpoint, preferable pluripotent stem cells is iPS cells.

(A) Step of Culturing Pluripotent Stem Cells (e.g., Human Pluripotent Stem Cells) in a Medium Containing a GSK-3 Beta Inhibitor or a GSK3-beta Inhibitor and a Retinoic Acid Derivative (First Step)

In this step, the human pluripotent stem cells obtained in the manner described above may be separated by any means and subjected to suspension culture or adhesion culture using a coated culture dish. In the present invention, adhesion culture is preferable. Examples of methods for dissociating human pluripotent stem cells include a mechanical method and a method using a dissociation solution having protease activity and collagenase activity (e.g., a solution containing Accutase™ and Accumax™) or a dissociation solution having collagenase activity alone (such separation solutions corresponding to reagents for monodispersing human pluripotent stem cells used in the present invention). Preferably, a dissociation solution having protease activity and collagenase activity is used to dissociate human pluripotent stem cells and mechanically and finely disperse the dissociated cells into single cells. Colonies that have been cultured to 80% confluence in the dish are preferably used as human pluripotent stem cells.

In suspension culture, cells are cultured without being adhered to a culture dish. Suspension culture can be carried out without particular limitation with the use of a culture dish that has not been artificially treated (e.g., by a coating treatment with an extracellular matrix), in order to improve adhesion of cells to the dish, or a culture dish that has been treated (e.g., by a coating treatment using polyhydroxyethyl methacrylate (poly-HEMA)) to artificially suppress adhesion.

In adhesion culture, cells are cultured in any medium in a coated culture dish. Examples of coating agents include Matrigel (BD), collagen, gelatin, laminin, heparan sulfate proteoglycan, entactin, and combinations of any thereof, with gelatin being preferable.

The medium used in this step can be prepared using a medium for animal cell culture as a basal medium. Examples of a basal medium include MEM, Medium 199, Eagle's Minimum Essential Medium (EMEM), alpha MEM, Dulbecco's modified Eagle's Medium (DMEM), Ham's F12 medium, RPMI 1640 medium, Fischer's medium, and a mixture of any thereof. A mixture of DMEM and F12 (1:1) is preferable. Such medium may or may not contain serum. Where needed, the medium may contain one or more serum substitutes selected from among, for example, albumin, transferrin, Knockout Serum Replacement (KSR) (which is a serum substitute for FBS upon ES cell culture), N2 supplement (Invitrogen), B27 supplement (Invitrogen), fatty acids, insulin, procollagens, trace elements, 2-mercaptoethanol, and 3'-thiolglycerol. A medium may further contain one or more substances selected from among, for example, lipids, amino acids, L-glutamine, Glutamax™ (Invitrogen), nonessential amino acids, vitamins, growth factors, low-molecular-weight compounds, antibiotics, antioxidants, pyruvate, buffering agents, and inorganic salts.

Examples of low-molecular-weight compounds include, but are not limited to, a GSK-3 beta inhibitor and a retinoic acid derivative.

A GSK-3 beta inhibitor is defined as a substance that blocks GSK-3 beta protein kinase activity (e.g., the capacity of beta catenin phosphorylation), and many such substances have already been known. Examples include the indirubin derivative BIO (another name: GSK-3 beta inhibitor IX; 6-bromoindirubin-3'-oxime), the maleimide derivative SB216763 (3-(2,4-dichlorophenyl)-4-(1-methyl-1H-indol-3-yl)-1H-pyrrole-2,5-dione), a phenyl alpha bromomethyl ketone compound (GSK-3 beta inhibitor VII; 4-dibromoacetophenone), cell membrane-permeable phosphorylated peptide (L803-mts; another name: GSK-3 beta peptide inhibitor; Myr-N-GKEAPPAPPQSpP-NH$_2$), and CHIR99021 (6-[2-[4-(2,4-dichlorophenyl)-5-(4-methyl-1H-imidazol-2-yl)pyrimidin-2-ylamino]ethylamino]pyridine-3-carbonitrile) with high selectivity. Such compounds are commercially and readily available from, for example, Calbiochem or Biomol., and such compounds may be obtained from other providers. Alternatively, a person skilled in the art may prepare such compound by him/herself.

A GSK-3 beta inhibitor usable in the present invention is preferably CHIR99021 represented by formula I.

Chem. 1

Chem. 1

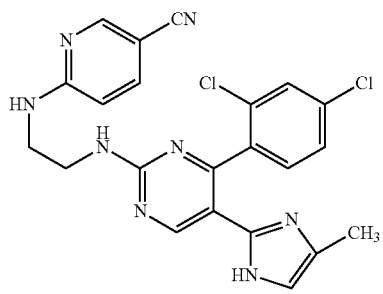

Formula I

CHIR99021 concentration in a medium is, for example, 100 nM, 500 nM, 750 nM, 1 micromolar, 2 micromolar, 3 micromolar, 4 micromolar, 5 micromolar, 6 micromolar, 7 micromolar, 8 micromolar, 9 micromolar, 10 micromolar, 15 micromolar, 20 micromolar, 25 micromolar, 30 micromolar, 40 micromolar, or 50 micromolar, although the concentration is not limited thereto. It is preferably 3 micromolar.

The term "retinoic acid derivative" refers to an artificially modified retinoic acid that retains the functions of a naturally-occurring retinoic acid. Examples thereof include AM580 (4-[[(5,6,7,8-tetrahydro-5,5,8,8-tetramethyl-2-naphthalenyl)carbonyl]amino]-benzoic acid) (Tamura, K. et al., Cell Differ. Dev. 32: 17-26, 1990), TTNPB (4-[(1E)-2-(5,6,7,8-tetrahydro-5,5,8,8-tetramethyl-2-naphthalenyl)-1-propen-1-yl]-benzoic acid) (Strickland, S. et al., Cancer Res. 43: 5268-5272, 1983), retinol palmitate, retinol, retinal, 3-dehydroretinoic acid, 3-dehydroretinol, 3-dehydroretinal, and compounds described in Abe, E. et al., Proc. Natl. Acad. Sci., U.S.A., 78: 4990-4994, 1981; Schwartz, E. L. et al., Proc. Am. Assoc. Cancer Res., 24: 18, 1983; and Tanenaga, K. et al., Cancer Res. 40: 914-919, 1980.

It is preferable that the retinoic acid derivative used in the present invention be AM580 represented by formula II or TTNPB represented by formula III.

Chem. 2

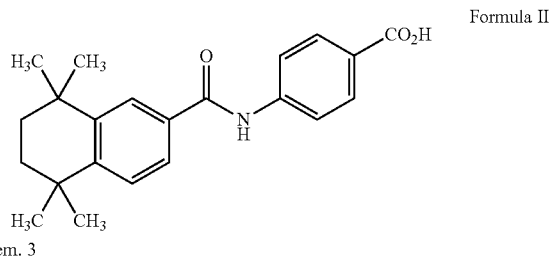

Formula II

Chem. 3

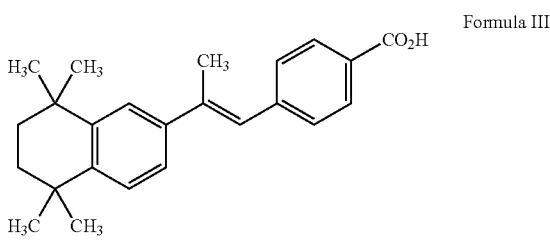

Formula III

AM580 concentration in a medium is, for example, 1 nM, 10 nM, 25 nM, 50 nM, 100 nM, 500 nM, 750 nM, 1 micromolar, 2 micromolar, 3 micromolar, 4 micromolar, 5 micromolar, 6 micromolar, 7 micromolar, 8 micromolar, 9 micromolar, 10 micromolar, 15 micromolar, 20 micromolar, 25 micromolar, 30 micromolar, 40 micromolar, or 50 micromolar, although the concentration is not limited thereto. It is preferably 1 micromolar.

TTNPB concentration in a medium is, for example, 1 nM, 10 nM, 25 nM, 50 nM, 100 nM, 500 nM, 750 nM, 1 micromolar, 2 micromolar, 3 micromolar, 4 micromolar, 5 micromolar, 6 micromolar, 7 micromolar, 8 micromolar, 9 micromolar, 10 micromolar, 15 micromolar, 20 micromolar, 25 micromolar, 30 micromolar, 40 micromolar, or 50 micromolar, although the concentration is not limited thereto. It is preferably 1 micromolar.

A medium used in this step may further comprise a Rho-associated coiled-coil forming kinase (ROCK) inhibitor. When this step comprises dispersing pluripotent stem cells into single cells, in particular, it is preferable that a medium comprise a ROCK inhibitor.

A ROCK inhibitor is defined as a substance that blocks kinase activity of Rho-kinase (ROCK). Examples include Y-27632 (4-[(1R)-1-aminoethyl]-N-pyridin-4-ylcyclohexane-1-carboxamide) or a dihydrochloride thereof (see, for example, Ishizaki et al., Mol. Pharmacol. 57, 976-983, 2000; Narumiya et al., Methods Enzymol. 325, 273-284, 2000), Fasudil/HA1077 (1-(5-isoquinolinesulfonyl)homopiperazine) or a dihydrochloride thereof (see, for example, Uenata et al., Nature 389: 990-994, 1997), H-1152 ((S)-(+)-2-methyl-1-[(4-methyl-5-isoquinolinyl)sulfonyl]-hexahydro-1H-1,4-diazepine) or a dihydrochloride thereof (see, for example, Sasaki et al., Pharmacol. Ther. 93: 225-232, 2002), Wf-536 ((+)-(R)-4-(1-aminoethyl)-N-(4-pyridyl)benzamide monohydrochloride) (see, for example, Nakajima et al., Cancer Chemother. Pharmacol. 52(4): 319-324, 2003), and a derivative of any thereof, an antisense nucleic acid, a nucleic acid inducing RNA interference (e.g., siRNA), a dominant-negative mutant against ROCK, and an expression vector for any thereof. Since other low-molecular-weight compounds are known as ROCK inhibitors, such compounds or derivatives thereof can also be used in the present invention (see, for example, US Patent Application Publication Nos. 20050209261, 20050192304, 20040014755, 20040002508, 20040002507, 20030125344, and 20030087919, and International Publication Nos. 2003/062227, 2003/059913, 2003/062225, 2002/076976, and 2004/039796). In the present invention, at least one type of ROCK inhibitor can be used.

It is preferable that a ROCK inhibitor used in the present invention be Y-27632 represented by formula IV.

Chem. 4

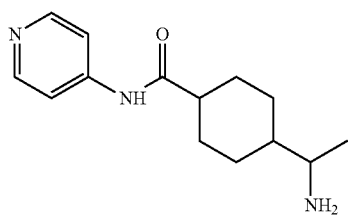

Formula IV

Y-27632 concentration in a medium is, for example, 100 nM, 500 nM, 750 nM, 1 micromolar, 2 micromolar, 3 micromolar, 4 micromolar, 5 micromolar, 6 micromolar, 7 micromolar, 8 micromolar, 9 micromolar, 10 micromolar, 15 micromolar, 20 micromolar, 25 micromolar, 30 micromolar, 40 micromolar, or 50 micromolar, although the concentration is not limited thereto. It is preferably 10 micromolar.

A person skilled in the art can readily replace substituents of low-molecular-weight compounds. For example, substituents can be replaced without particular limitation, provided that properties of the compounds (e.g., a GSK-3 beta inhibitor, a retinoic acid derivative, and a ROCK inhibitor) described above are maintained.

Examples of media preferably used in the present step include a DMEM/F12 medium containing Glutamax (Invitrogen), FBS (Hyclone), PenStrep, Y-27632, and CHIR99021 and a DMEM/F12 medium containing Glutamax (Invitrogen), FBS (Hyclone), PenStrep, Y-27632, CHIR99021, and AM580 or TTNPB.

Culture is carried out at about 30 degrees C. to 40 degrees C., and preferably at about 37 degrees C. under an atmosphere of air containing $CO_2$ although the temperature is not limited thereto. The $CO_2$ concentration ranges from about 2% to 5%, with 5% being preferable. Culture is carried out for up to 2 days, for example, with 2 days being preferable. A cell population (cell mass) is generated via suspension culture of human pluripotent stem cells.

(B) Step of Culturing Pluripotent Stem Cells (e.g., Human Pluripotent Stem Cells) in Medium Containing Retinoic Acid Derivative (Second Step)

In this step, the cell population after suspension culture obtained in the first step may be cultured in such state in any medium in a coated culture dish. Examples of coating agents include collagen, gelatin, laminin, heparan sulfate proteoglycan, entactin, and a combination of any thereof, with gelatin being preferable.

Alternatively, in this step, the cells obtained by adhesion culture in the first step may be continuously cultured while the medium is exchanged with fresh medium.

The medium used in this step can be prepared using a medium for animal cell culture as a basal medium. Examples of a basal medium include IMDM, Medium 199, Eagle's Minimum Essential Medium (EMEM), alpha MEM, Dulbecco's modified Eagle's Medium (DMEM), Ham's F12 medium, RPMI 1640 medium, Fischer's medium, and a mixture of any thereof. A mixture of DMEM and F12 (1:1) is preferable. A preferable medium is serum-free. Where necessary, the medium may contain one or more serum substitutes selected from among, for example, albumin, transferrin, sodium selenite, ITS-X (Invitrogen) (containing insulin, transferrin, and sodium selenite), Knockout Serum Replacement (KSR) (which is a serum substitute for FBS upon ES cell culture), N2 supplement (Invitrogen), B27 supplement (Invitrogen), fatty acids, insulin, procollagens, trace elements, 2-mercaptoethanol, and 3'-thiolglycerol. The medium may further contain one or more substances selected from among, for example, lipids, amino acids, L-glutamine, Glutamax, nonessential amino acids, vitamins, growth factors, low-molecular-weight compounds, antibiotics, antioxidants, pyruvate, buffering agents, and inorganic salts. An example of a low-molecular-weight compound is, but is not limited to, a retinoic acid derivative.

The term "retinoic acid derivative" refers to an artificially modified retinoic acid that retains the functions of a naturally-occurring retinoic acid. Examples thereof include AM580 (4-[[(5,6,7,8-tetrahydro-5,5,8,8-tetramethyl-2-naphthalenyl)carbonyl]amino]-benzoic acid) (Tamura, K. et al., Cell Differ. Dev. 32: 17-26, 1990), TTNPB (4-[(1E)-2-(5,6,7,8-tetrahydro-5,5,8,8-tetramethyl-2-naphthalenyl)-1-propen-1-yl]-benzoic acid) (Strickland, S. et al., Cancer Res. 43: 5268-5272, 1983), and compounds described in Abe, E. et al., Proc. Natl. Acad. Sci., U.S.A., 78: 4990-4994, 1981; Schwartz, E. L. et al., Proc. Am. Assoc. Cancer Res., 24: 18, 1983; and Tanenaga, K. et al., Cancer Res. 40: 914-919, 1980.

It is preferable that the retinoic acid derivative used in the present invention be AM580 represented by formula V or TTNPB represented by formula VI.

Chem. 5

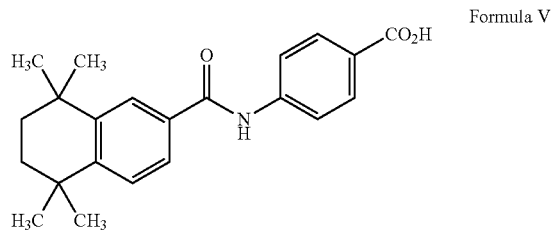

Formula V

Chem. 6

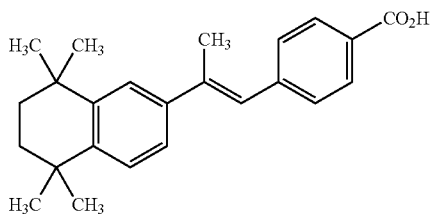

Formula VI

AM580 concentration in a medium is, for example, 1 nM, 10 nM, 25 nM, 50 nM, 100 nM, 500 nM, 750 nM, 1 micromolar, 2 micromolar, 3 micromolar, 4 micromolar, 5 micromolar, 6 micromolar, 7 micromolar, 8 micromolar, 9 micromolar, 10 micromolar, 15 micromolar, 20 micromolar, 25 micromolar, 30 micromolar, 40 micromolar, or 50 micromolar, although the concentration is not limited thereto. It is preferably 1 micromolar.

TTNPB concentration in a medium is, for example, 1 nM, 10 nM, 25 nM, 50 nM, 100 nM, 500 nM, 750 nM, 1 micromolar, 2 micromolar, 3 micromolar, 4 micromolar, 5 micromolar, 6 micromolar, 7 micromolar, 8 micromolar, 9 micromolar, 10 micromolar, 15 micromolar, 20 micromolar, 25 micromolar, 30 micromolar, 40 micromolar, or 50 micromolar, although the concentration is not limited thereto. It is preferably 1 micromolar.

An example of a medium preferably used in this step is a DMEM/F12 medium containing 2-mercaptoethanol, Glutamax, KNOCKOUT™ SR, MEM NEAA, PenStrep, and AM580 or TTNPB.

Culture is carried out at about 30 degrees C. to 40 degrees C., and preferably at about 37 degrees C. under an atmosphere of air containing $CO_2$. The $CO_2$ concentration ranges from about 2% to 5%, with 5% being preferable. Culture is carried out for at least 3 days, for example, with 3 or 8 days being preferable. When culture is continued for 8 days, the medium is preferably exchanged with fresh medium every 3 days. Intermediate mesoderm cells are induced via the adhesion culture.

<Method for Producing Metanephric Cells>

In the present invention, the induced intermediate mesoderm cells may be induced to differentiate into metanephric cells by further continuing adhesion culture.

The term "metanephric cell" used herein refers to a cell contained within metanephron, and it preferably refers to a cell selected form the group consisting of metanephric mesenchyme cell, metanephric stroma cell, ureteric bud cell, podocyte and proximal tubule cell. In the present invention, the metanephric mesenchyme cell preferably expresses SIX2 (e.g. NCBI Accession No: NM_016932) and/or HOXD11 (e.g. NCBI Accession No: NM_021192), metanephric stroma cell preferably expresses FOXD1 (e.g. NCBI Accession No: NM_004472), ureteric bud cell preferably expresses SALL4 (e.g. NCBI Accession No: NM_020436) and/or C-RET (e.g. NCBI Accession No: NM_020630) and/or HOXB7 (e.g. NCBI Accession No: NM_004502), podocyte preferably expresses PODOCALYXIN (e.g. NCBI Accession No: NM_005397 or NM_001018111), and proximal tubule cell preferably expresses E-cadherin (e.g. NCBI Accession No: NM_004360).

The medium used in the adhesion culture can be prepared using a medium for animal cell culture as a basal medium. Examples of a basal medium include MEM, Medium 199, Eagle's Minimum Essential Medium (EMEM), alpha MEM, Dulbecco's modified Eagle's Medium (DMEM), Ham's F12 medium, RPMI 1640 medium, Fischer's medium, and a mixture of any thereof. A mixture of DMEM and F12 (1:1) is preferable. A preferable medium is serum-free. Where necessary, the medium may contain one or more serum substitutes selected from among, for example, albumin, transferrin, sodium selenite, ITS-X (Invitrogen) (containing insulin, transferrin, and sodium selenite), Knockout Serum Replacement (KSR) (which is a serum substitute for FBS upon ES cell culture), N2 supplement (Invitrogen), B27 supplement (Invitrogen), fatty acids, insulin, procollagens, trace elements, 2-mercaptoethanol, and 3'-thiolglycerol. The medium may further contain one or more substances selected from among, for example, lipids, amino acids, L-glutamine, Glutamax, nonessential amino acids, vitamins, growth factors, antibiotics, antioxidants, pyruvate, buffering agents, and inorganic salts. An example of the growth factors is, but is not limited to, Wnt3a and BMP7. An example of a medium preferably used in this step is DMEM/F12 medium containing KSR, Glutamax, amino acid, Wnt3a and BMP7.

Culture is carried out at about 30 degrees C. to 40 degrees C., and preferably at about 37 degrees C. under an atmosphere of air containing $CO_2$. The $CO_2$ concentration ranges from about 2% to 5%, with 5% being preferable. Culture is carried out for up to 5 days, for example, with 5, 6, 7, 8 days or more being preferable. More preferably, the culture term is 8 days.

In the present invention, before further adhesion culture, the induced intermediate mesoderm cells may be isolated from other type cells by using OSR1 as a marker. In this isolation step, but are not limited to, flow cytometer may be used.

<Method for Producing Luminal Structure Constructed with Renal Tubule Cells by Forming Sphere>

In one embodiment, the luminal structure constructed with renal tubule cells may be produced by forming sphere consisting of above induced intermediate mesoderm cell.

The term "the renal tubule cell" used herein refers to the cells binding with LTL (Lotus Tetragonolobus Lectin) and/or expressing E-cadherin (e.g. NCBI Accession No: NM_004360). More preferably, the renal tubule is proximal tubule.

In this producing step, the intermediate mesoderm cell may be subjected to suspension culture to form sphere. In suspension culture, cells are cultured without being adhered to a culture dish. Suspension culture can be carried out without particular limitation with the use of a culture dish that has not been artificially treated (e.g., by a coating treatment with an extracellular matrix), in order to improve adhesion of cells to the dish, or a culture dish that has been treated (e.g., by a coating treatment using polyhydroxyethyl methacrylate (poly-HEMA) or PrimeSurface (Sumitomo Bakelite co.)) to artificially suppress adhesion.

The medium used in the suspention culture can be prepared using a medium for animal cell culture as a basal medium. Examples of a basal medium include MEM, Medium 199, Eagle's Minimum Essential Medium (EMEM), alpha MEM, Dulbecco's modified Eagle's Medium (DMEM), Ham's F12 medium, RPMI 1640 medium, Fischer's medium, and a mixture of any thereof. A mixture of DMEM and F12 (1:1) is preferable. A preferable medium is serum-free. Where necessary, the medium may contain one or more serum substitutes selected from among, for example, albumin, transferrin, sodium selenite, ITS-X (Invitrogen) (containing insulin, transferrin, and sodium selenite), Knockout Serum Replacement (KSR) (which is a serum substitute for FBS upon ES cell culture), N2 supplement (Invitrogen), B27 supplement (Invitrogen), fatty acids, insulin, procollagens, trace elements, 2-mercaptoethanol, and 3'-thiolglycerol. The medium may further contain one or more substances selected from among, for example, lipids, amino acids, L-glutamine, Glutamax, nonessential amino acids, vitamins, growth factors, antibiotics, antioxidants, pyruvate, buffering agents, and inorganic salts. An example of a medium preferably used in this step is DMEM/F12 medium containing KSR, Glutamax, and amino acid.

The suspension culture is carried out at about 30 degrees C. to 40 degrees C., and preferably at about 37 degrees C. under an atmosphere of air containing $CO_2$. The $CO_2$ concentration ranges from about 2% to 5%, with 5% being preferable. The suspension culture is carried out for up to 5 days, for example, with 5, 6, 7, 8 days or more being preferable. More preferably, the suspension culture is carried out for 8 days.

In the present invention, before further adhesion culture, the induced intermediate mesoderm cells may be isolated from other type cells by using OSR1 as a marker. In this isolation step, but are not limited to, flow cytometer may be used.

<Method for Producing Luminal Structure Constructed with Renal Tubule Cells by Organ Culture>

In another embodiment, the luminal structure constructed with renal tubule cells may be produced by culturing above induced intermediate mesoderm cell with metanephric cells derived from mouse embryos.

In this producing step, the intermediate mesoderm cell may be subjected to co-culture with metanephric cell derived from mouse embryos. In the co-culture, to form cell cluster, the cells are cultured without being adhered to a culture dish. The co-culture can be carried out without particular limitation with the use of a culture dish that has not been artificially treated (e.g., by a coating treatment with an extracellular matrix), in order to improve adhesion of cells to the dish, or a culture dish that has been treated (e.g., by a coating treatment using polyhydroxyethyl methacrylate (poly-HEMA) or PrimeSurface (Sumitomo Bakelite co.)) to artificially suppress adhesion.

After forming cell cluster, the cell cluster is cultured with organ culture method. The organ culture method may be carried out in a conventional manner well known to one of ordinary skill in the art, like as the method described in Kanwar Y S et al., Am J Physiol Renal Physiol. 282, F953-965, 2002. Preferably, the cell cluster may be cultured on the filter with pore, wherein the filter is floating on the medium.

The medium used in the co-culture and organ culture can be prepared using a medium for animal cell culture as a basal medium. Examples of a basal medium include MEM, Medium 199, Eagle's Minimum Essential Medium (EMEM), alpha MEM, Dulbecco's modified Eagle's Medium (DMEM), Ham's F12 medium, RPMI 1640 medium, Fischer's medium, and a mixture of any thereof. MEM medium is preferable. Where necessary, the medium may contain serum or one or more serum substitutes selected from among, for example, albumin, transferrin, sodium selenite, ITS-X (Invitrogen) (containing insulin, transferrin, and sodium selenite), Knockout Serum Replacement (KSR) (which is a serum substitute for FBS upon ES cell culture), N2 supplement (Invitrogen), B27 supplement (Invitrogen), fatty acids, insulin, procollagens, trace elements, 2-mercaptoethanol, and 3'-thiolglycerol. The medium may further contain one or more substances selected from among, for example, lipids, amino acids, L-glutamine, Glutamax, nonessential amino acids, vitamins, growth factors, antibiotics, antioxidants, pyruvate, buffering agents, and inorganic salts. An example of a medium preferably used in this step is MEM medium containing serum.

The culture is carried out at about 30 degrees C. to 40 degrees C., and preferably at about 37 degrees C. under an atmosphere of air containing $CO_2$. The $CO_2$ concentration ranges from about 2% to 5%, with 5% being preferable. The co-culture to form cell cluster is carried out for up to 1 days, for example, with 1, 2, 3, 4 days or more being preferable. The organ culture for cell cluster is carried out for up to 5 days, for example, with 5, 6, 7, 8, 9, 10 days or more being preferable. More preferably, the organ culture is carried out for 7 days.

In the co-culture, ratio of induced intermediate mesoderm cell to metanephric cells derived from mouse embryos may be 1 to 10. An example of preferable number of intermediate mesoderm cells are $1 \times 10^4$ cells, and corresponding number of metanephric cells are $1 \times 10^5$ cells.

In the present invention, metanephric cells derived from mouse embryos may be obtained from E11.5, E12.5, E13.5 or E14.5 mouse embryos. More preferably, E11.5 mouse embryos are used in this step.

In the present invention, before co-culture, the induced intermediate mesoderm cells may be isolated from other type cells by using OSR1 as a marker. In this isolation step, but are not limited to, flow cytometer may be used.

<Kit for Inducing Differentiation of Pluripotent Stem Cells into Intermediate Mesoderm Cells>

The present invention provides a kit for inducing differentiation of pluripotent stem cells into intermediate mesoderm cells. The kit may comprise a compound used for induction of differentiation mentioned above, a culture solution, a dissociation solution (including a reagent for monodispersing human pluripotent stem cells), and an agent for coating a culture dish. The kit may further comprise written procedures or instructions for induction of differentiation.

<Intermediate Mesoderm Cells>

The present invention provides intermediate mesoderm cells prepared by the above method for induction of differentiation. Intermediate mesoderm cells can be identified using markers for intermediate mesoderm cells, such as OSR1, PAX2, WT1, EYA1, and SIX2.

<Luminal Structure Constructed with Renal Tubule Cells>

The luminal structure constructed with renal tubule cells provided in this invention may be used for drug screening assay or graft treatment.

EXAMPLES

Hereafter, the present invention is described in greater detail with reference to the Examples, although the technical scope of the present invention is not limited to the Examples below.

Establishment of OSR1-GFP-knocked-in Human iPS Cell Line

Human iPS cells (201B7) provided by Dr. Yamanaka at Kyoto University were cultured by the known method (Takahashi, K. et al., Cell 131: 861-872). Subsequently, a GFP-PGK-Neo cassette was inserted into a site downstream of the OSR1 initiation codon of a BAC clone (RP11-458J18) (BACPAC RESOURCES) using pRed/ET (Gene Bridges GmbH), so as to prepare a OSR1-GFP BAC transgene. The resulting modified BAC clone was introduced into the human iPS cell and the OSR1-GFP reporter iPS cell line expressing GFP in conjunction with the expression of endogenous OSR1 was established.

Comparative Example 1

Induction of Differentiation into Intermediate Mesoderm Cells (Known Method: International Patent Application No. PCT/JP2011/067181 (WO 2012/011610))

The above OSR1-GFP reporter iPS cells were cultured to confluence on a 10-cm dish using SNL cells as feeder cells (McMahon, A. P. and Bradley, A., 1990, Cell 62; 1073-1085). A CTK solution was added to the cells for dissociation, the feeder cells were removed, and the iPS cells were dispersed into single cells with the addition of Accutase.

Subsequently, the iPS cells were suspended in a DMEM/F12 medium containing Glutamax (Invitrogen), 2% FBS (Hyclone), and PenStrep, and 10 micromolar Y-27632, 3 micromolar CHIR99021, and 100 ng/ml Activin A were added thereto. The cell suspension was then transferred to a dish coated with 0.1% gelatin, and culture was conducted for 2 days.

Thereafter, the medium was removed, the culture product was washed in PBS, and the iPS cells were then cultured for an additional 8 days in a medium prepared by adding 3 micromolar CHIR99021 and 100 ng/ml BMP7 to a DMEM/F12 medium containing 2-mercaptoethanol, Glutamax, 10% KOCKOUT SR (Invitrogen), 0.1 mM MEM NEAA, and PenStrep. During culture, the medium was exchanged with fresh medium once every 3 days.

Example 1

Induction of Differentiation into Intermediate Mesoderm Cells (Novel Induction Method 1)

The above OSR1-GFP reporter iPS cells were cultured to confluence on a 10-cm dish using SNL cells as feeder cells (McMahon, A. P. and Bradley, A., 1990, Cell 62; 1073-1085). A CTK solution was added to the cells for dissociation, the feeder cells were removed, and the iPS cells were dispersed into single cells with the addition of Accutase.

Subsequently, the iPS cells were suspended in a DMEM/F12 medium containing Glutamax, 2% FBS, and PenStrep, and 10 micromolar Y-27632 and 3 micromolar CHIR99021 were added thereto. Subsequently, the cell suspension was transferred to a dish coated with 0.1% gelatin, and culture was conducted for 2 days.

Thereafter, the medium was removed, the culture product was washed in PBS, and the iPS cells were then cultured for an additional 8 days in a medium prepared by adding 1 micromolar AM580 or 1 micromolar TTNPB to a DMEM/F12 medium containing 2-mercaptoethanol, Glutamax, 10% KOCKOUT SR, 0.1 mM MEM NEAA, and PenStrep. During culture, the medium was exchanged with fresh medium once every 3 days.

After the cell culture had been conducted for 8 days, the cells were analyzed by flow cytometry (FACS) using OSR1 expression as an indicator. The results demonstrate that OSR1-positive cells were successfully induced by the above-described method (FIG. 1).

Example 2

Induction of Differentiation into Intermediate Mesoderm Cells (Novel Induction Methods 2 and 3)

The above OSR1-GFP reporter iPS cells were cultured to confluence on a 10-cm dish using SNL cells as feeder cells (McMahon, A. P. and Bradley, A., 1990, Cell 62; 1073-1085). A CTK solution was added to the cells for dissociation, the feeder cells were removed, and the iPS cells were dispersed into single cells with the addition of Accutase.

Subsequently, the iPS cells were suspended in a DMEM/F12 medium containing Glutamax, 2% FBS, and PenStrep, and a combination of (1) 10 micromolar Y-27632 (ROCK inhibitor), 3 micromolar CHIR99021, and 1 micromolar AM580 or (2) 10 micromolar Y-27632 (ROCK inhibitor), 3 micromolar CHIR99021, and 1 micromolar TTNPB was added thereto. Subsequently, the cell suspension was transferred to a dish coated with 0.1% gelatin, and culture was conducted for 2 days.

Thereafter, the medium was removed, the culture product was washed in PBS, and the iPS cells were then cultured for an additional 8 days (novel induction method 2) or 3 days (novel induction method 3) in a medium prepared by adding 1 micromolar AM580 or 1 micromolar TTNPB to a DMEM/F12 medium containing 2-mercaptoethanol, Glutamax, 10% KOCKOUT SR, 0.1 mM MEM NEAA, and PenStrep. During culture, the medium was exchanged with fresh medium once every 3 days in the case of the novel induction method 2.

Figure 2:
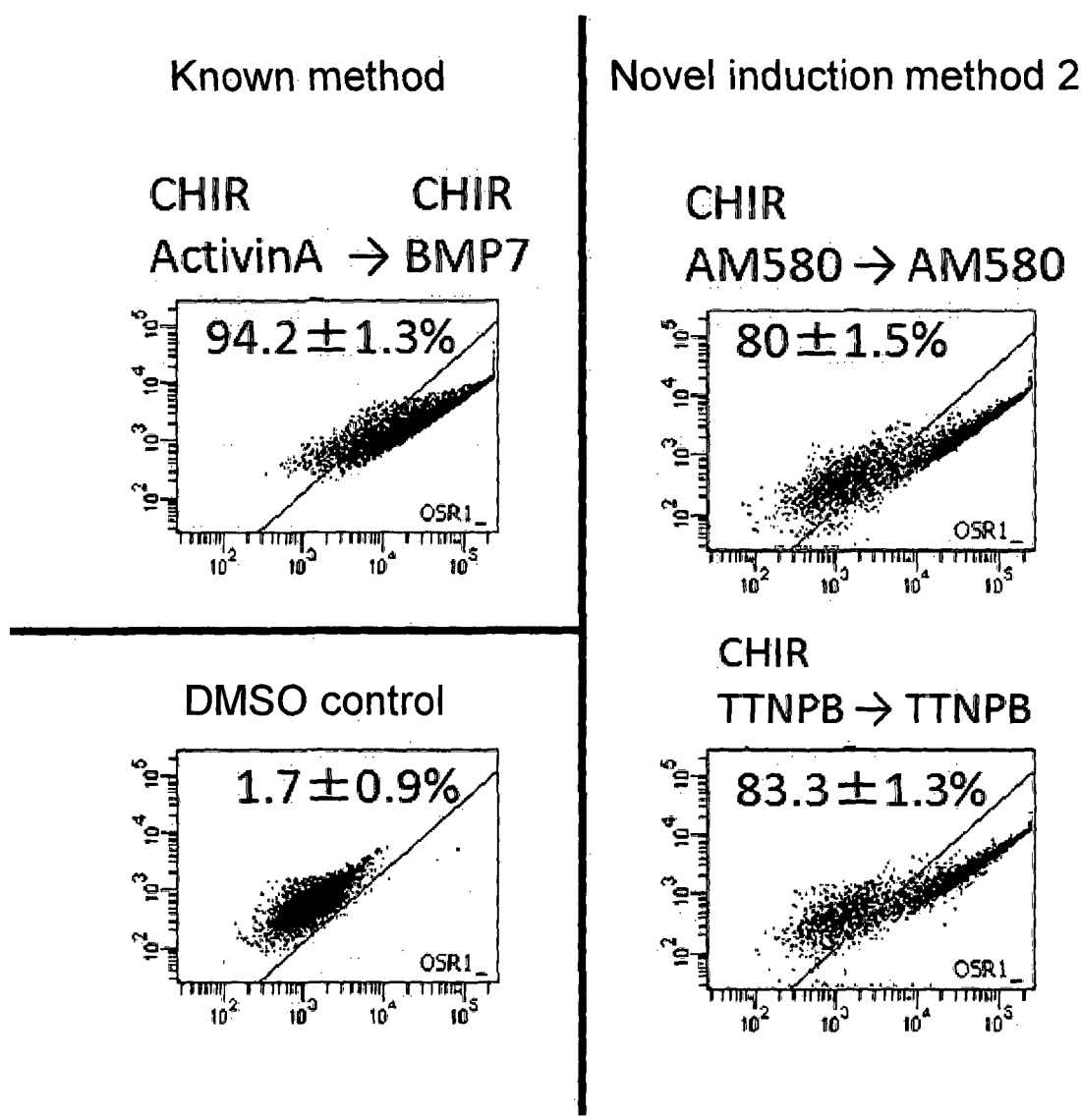
FIG. 2 shows the results of flow cytometric analysis of the cells obtained by inducing differentiation of the iPS cells on day 11 by the following methods using OSR1 (GFP) expression as the indicator: a method in which a medium containing CHIR99021 and Activin A is exchanged with a medium containing CHIR99021 and BMP7 (known method, upper left); a control method in which a medium supplemented with DMSO is used (DMSO control, lower left); and a method in which a medium containing CHIR99021 and AM580 or TTNPB is exchanged with a medium containing AM580 (upper right) or TTNPB (lower right) (novel induction method 2). Numerals in the figure indicate percentages of OSR1-positive cells.
Figure 3:
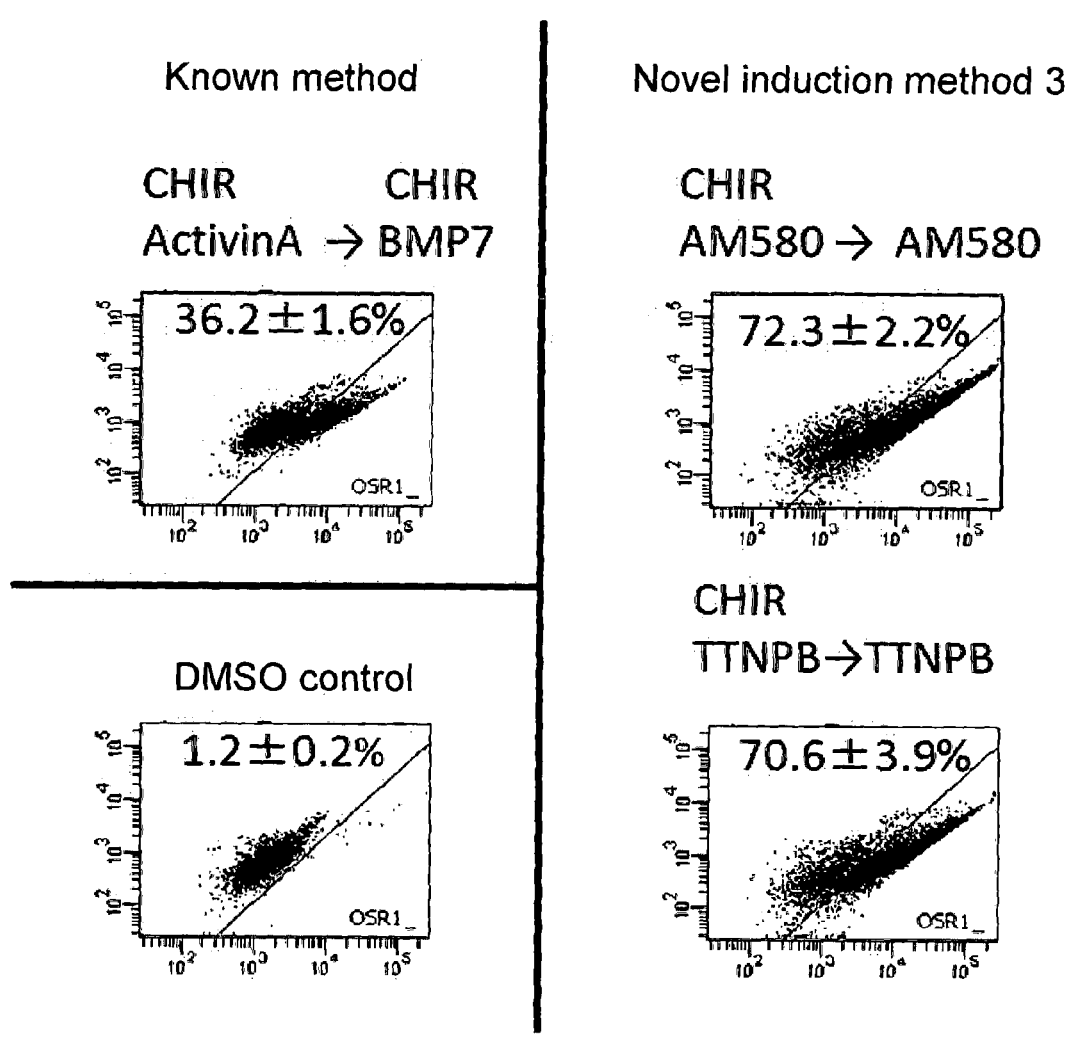
FIG. 3 shows the results of flow cytometric analysis of the cells obtained by inducing differentiation of the iPS cells on day 6 by the following methods using OSR1 (GFP) expression as the indicator: a method in which a medium containing CHIR99021 and Activin A is exchanged with a medium containing CHIR99021 and BMP7 (known method, upper left); a control method in which a medium supplemented with DMSO is used (DMSO control, lower left); and a method in which a medium containing CHIR99021 and AM580 or TTNPB is exchanged with a medium containing AM580 (upper right) or TTNPB (lower right) (novel induction method 3). Numerals in the figure indicate percentages of OSR1-positive cells.

After the cell culture had been conducted for 8 or 3 days, the cells were analyzed by flow cytometry (FACS) using OSR1 expression as an indicator. The results demonstrate that OSR1-positive cells were successfully induced by the above-described methods (FIGS. 2 and 3).

Figure 4:
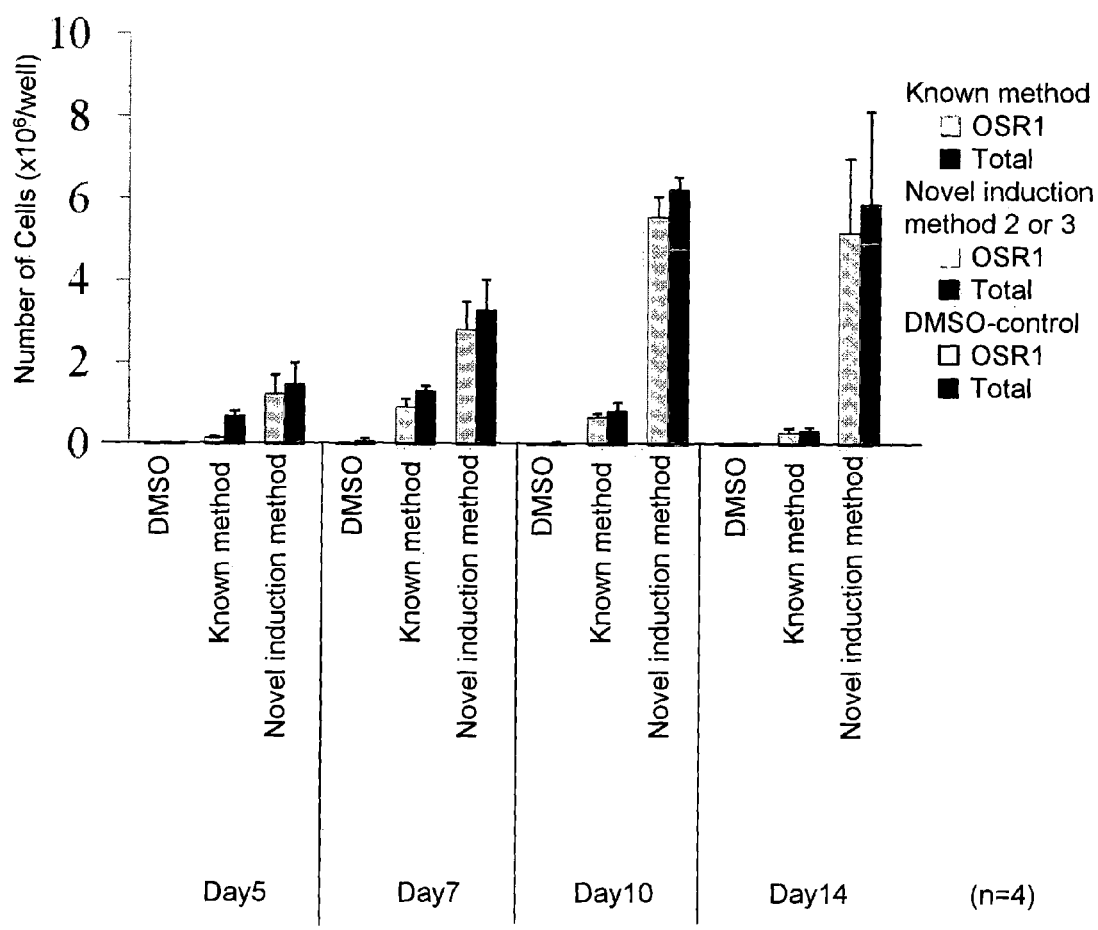
FIG. 4 shows the graph indicating number of cells on several conditions. DMSO is negative control. OSR1 means OSR1 positive cells. Total means all cells including OSR1 positive cells and OSR1 negative cells. Novel induction method means the method in which a medium containing CHIR99021 and TTNPB is exchanged with a medium containing TTNPB. "Day" indicates culture period.

Next, the length of time from medium change was studied. Briefly, number of OSR1 positive cells and total cells were measured at 3 days (novel induction method 3), 5 days, 8 days (novel induction method 2) or 12 days after the medium was changed to a medium prepared by adding 1 micromolar AM580 or 1 micromolar TTNPB to a DMEM/F12 medium containing 2-mercaptoethanol, Glutamax, 10% KOCKOUT SR, 0.1 mM MEM NEAA, and PenStrep (FIG. 4). The growth of OSR1 positive cells had plateau at 8 day after the medium change.

Figure 5:
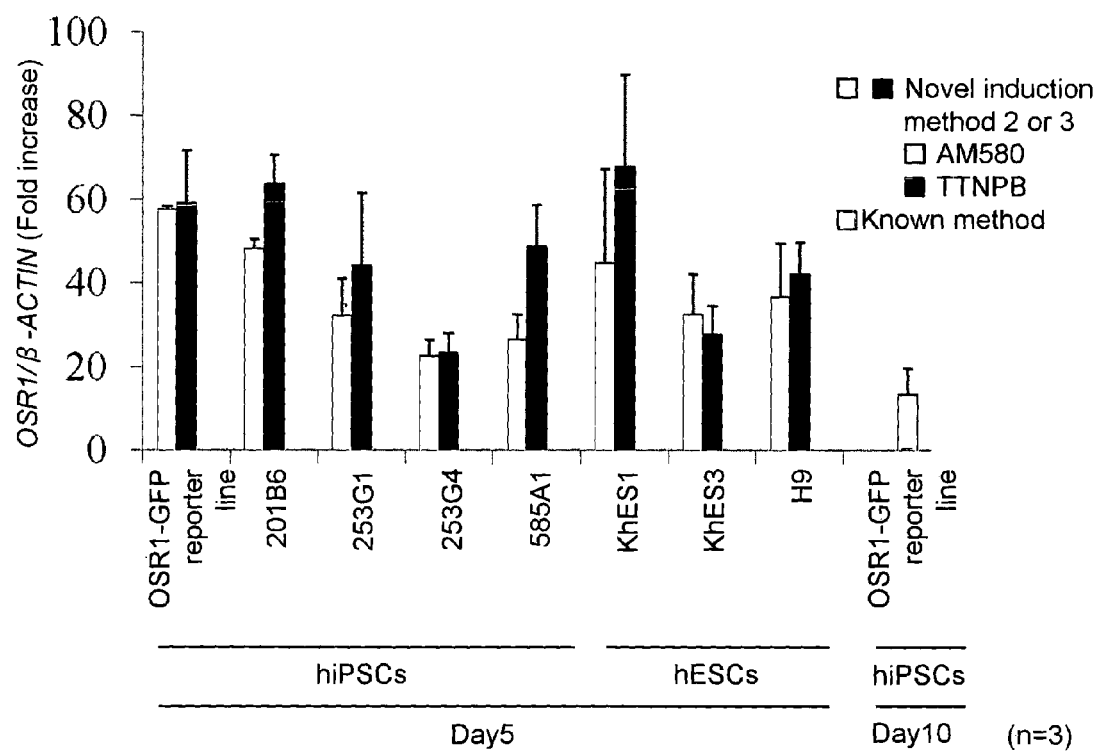
FIG. 5 shows the graph indicating level of OSR1 expression after differentiation from each iPS cell clone or ES clone. White bar indicates the result using AM580. Black bar indicates the result using TTNPB. Grey bar indicate the result of conventional method without AM580 and TTNPB.

Several iPS cell clones (201B6, 253G1, 263G4 and 585A1) and ES cell clone (KhES1, KhES3 and H9) could be differentiated into intermediate mesoderm cells by the novel induction method 3 (FIG. 5).

Figure 6:
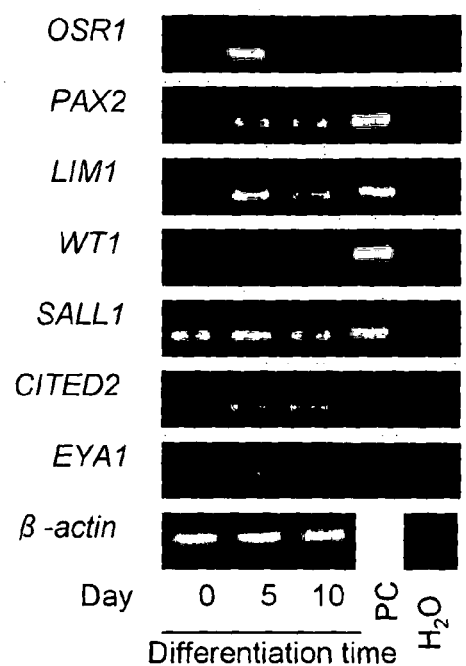
FIG. 6A shows the result of PCR analysis for cells differentiated with novel induction method 2 (6 days) and 3 (11 days).
FIG. 6B shows the result of in situ hybridization (upper panel) and immunostaining (lower panel) for cells differentiated with novel induction method 2 (6 days).
Figure 6:
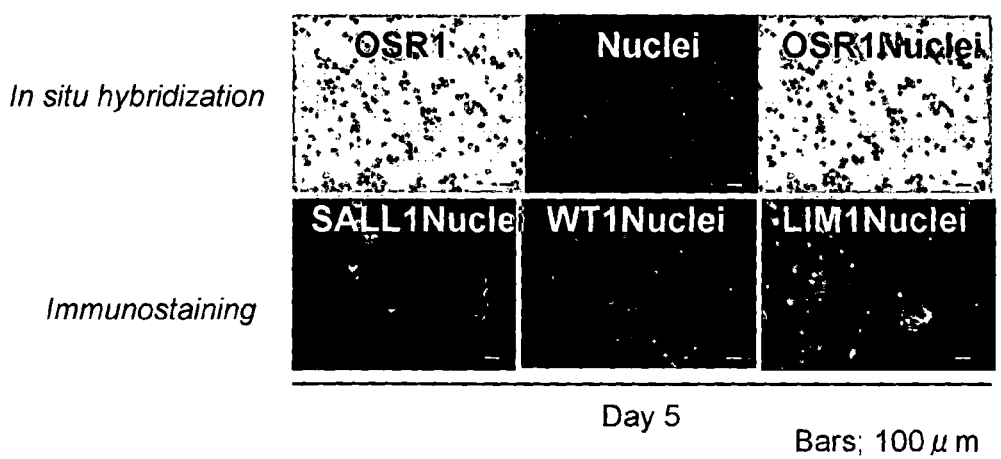

Furthermore, other intermediate mesoderm cell markers (like as PAX2, LIM1, WT1, SALL1, CITED2 and EYA1) were expressed in the OSR1 positive cells produced by the novel induction method 2 or 3 (FIGS. 6A and B).

Example 3

Long Term Culture

Figure 7:
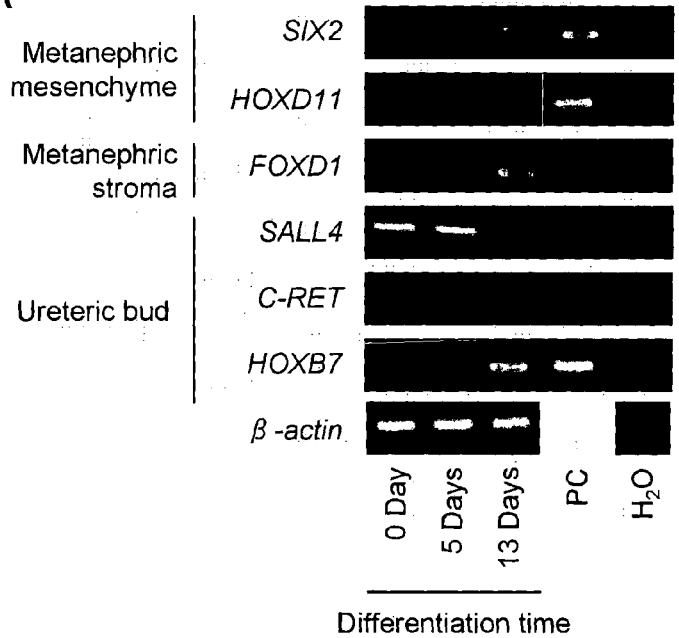
FIG. 7A shows the result of PCR analysis for cells differentiated with long term culture indicated as 13 Days.
FIG. 7B shows the result of immunostaining.
Figure 7:
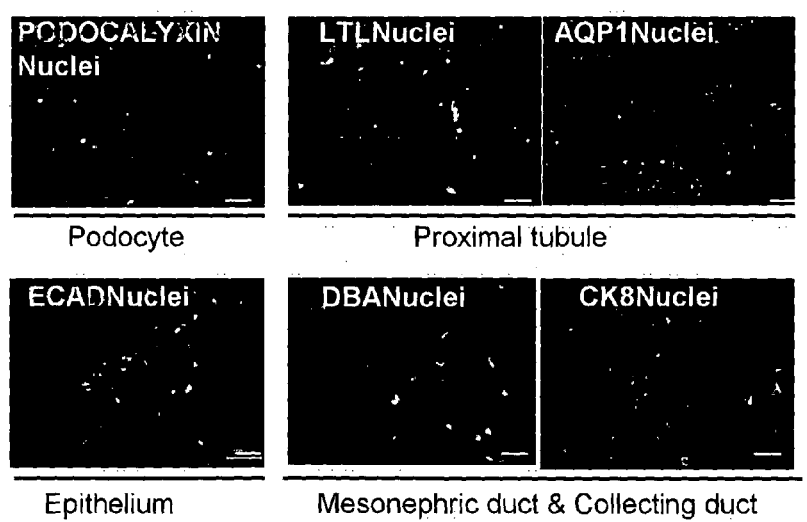

The above OSR1-GFP reporter iPS cells were dissociated into single cells in a manner similar to Example 2. Subsequently, the iPS cells were suspended in a DMEM/F12 medium containing Glutamax, 2% FBS, and PenStrep, and a combination of 10 micromolar Y-27632, 3 micromolar CHIR99021, and 1 micromolar TTNPB was added thereto. Subsequently, the cell suspension was transferred to a dish coated with 0.1% gelatin, and culture was conducted for 2 days. Thereafter, the medium was removed, the culture product was washed in PBS, and the iPS cells were then cultured for an additional 3 days (novel induction method 3) in a medium prepared by adding 1 micromolar TTNPB to a DMEM/F12 medium containing 2-mercaptoethanol, Glutamax, 10% KOCKOUT SR, 0.1 mM MEM NEAA, and PenStrep. After isolating GFP positive cells from obtained cells with flow cytometer, the GFP positive cells were transferred to a dish coated with Matrigel (BD), and cultured in DMEM/F12 medium containing 10 micromolar Y-27632, 100 ng/ml BMP7, 100 ng/ml Wnt3a, 2-mercaptoethanol, Glutamax, 10% KOCKOUT SR, 0.1 mM MEM NEAA, and PenStrep for 8 days. During culture, the medium was exchanged with fresh medium once every 3 days. Obtained cells were analyzed with RT-PCR (FIG. 7A) and immunostaining (FIG. 7B). As a result, obtained OSR1 positive cells could be further differentiated into renal precursor cells including metanephric mesenchyme, metanephric stroma or ureteric bud. Furthermore, there were the cells constructing kidney or generating in developmental process like as podocyte, proximal tubule, epithelium, mesonephric suet and collecting duct after long term differentiation. It was confirmed that the OSR1 positive cells had the potential to develop into kidney cells.

Example 4

Suspention Culture

The above OSR1-GFP reporter iPS cells were dispersed into single cells in a manner similar to Example 2. Subsequently, the iPS cells were suspended in a DMEM/F12 medium containing Glutamax, 2% FBS, and PenStrep, and a combination of 10 micromolar Y-27632, 3 micromolar CHIR99021, and 1 micromolar TTNPB was added thereto. Subsequently, the cell suspension was transferred to a dish coated with 0.1% gelatin, and culture was conducted for 2 days. Thereafter, the medium was removed, the culture product was washed in PBS, and the iPS cells were then cultured for an additional 3 days (novel induction method 3) in a medium prepared by adding 1 micromolar TTNPB to a DMEM/F12 medium containing 2-mercaptoethanol, Glutamax, 10% KOCKOUT SR, 0.1 mM MEM NEAA, and PenStrep. After isolating GFP positive cells from obtained cells with flow cytometer, $1 \times 10^5$ GFP positive cells were transferred to a low cell adhesion plate (PrimeSurface, Sumitomo Bakelite co.), and cultured in DMEM/F12 medium containing 10 micromolar Y-27632, 2-mercaptoethanol, Glutamax, 10% KOCKOUT SR, 0.1 mM MEM NEAA, and PenStrep in suspension to form cell sphere. During culture, the medium was exchanged with fresh medium once every 3 days.

Figure 8:
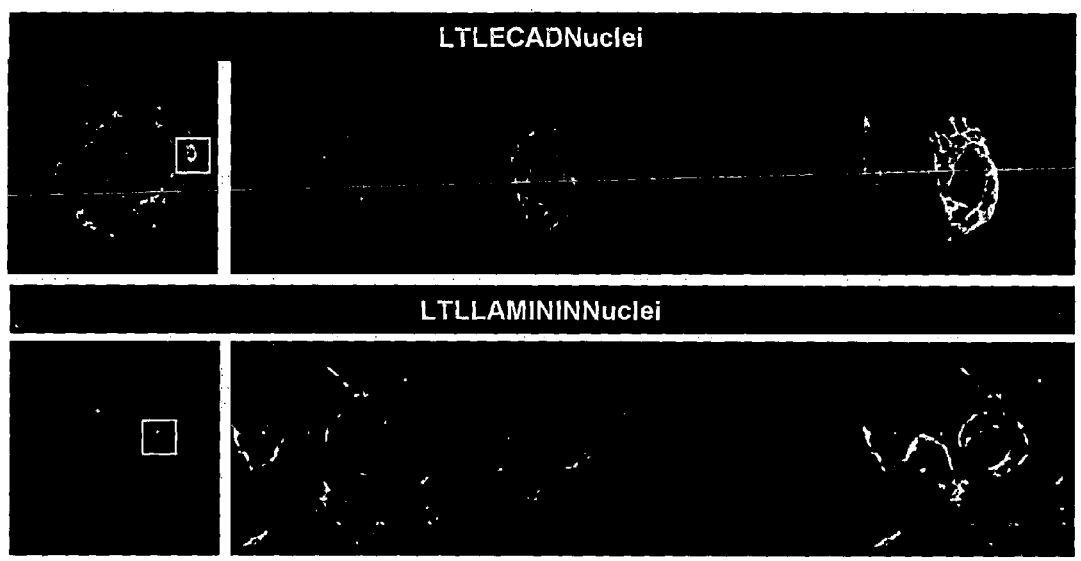
FIG. 8 shows the result of immunostaining for cells differentiated with suspension culture.

Obtained cells were analyzed with immunostaining (FIG. 8). It was confirmed that luminal structure could be constructed with renal tubule differentiated from the OSR1 positive cells by forming sphere.

Example 5

Organ Culture

Figure 9:
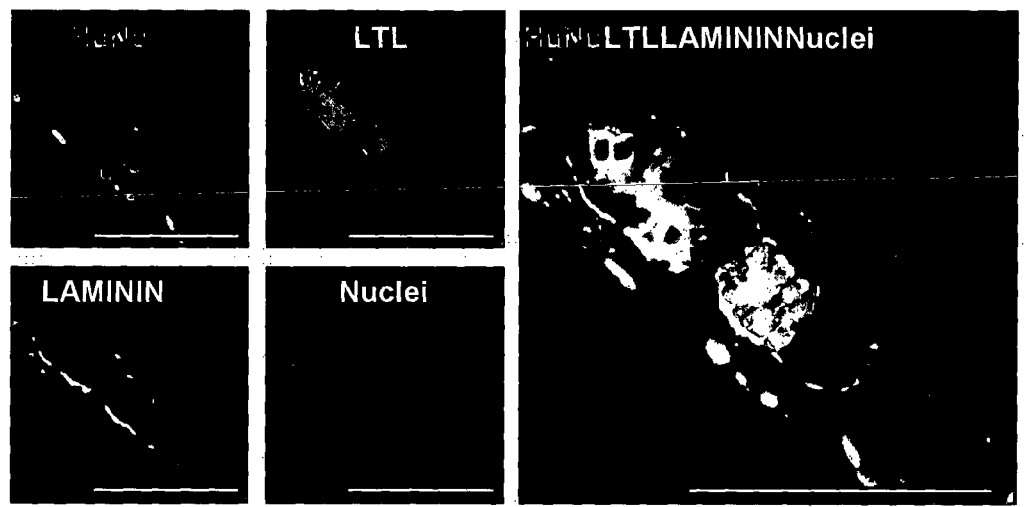
FIG. 9 shows the result of immunostaining for cells differentiated with organ culture.

The above OSR1-GFP reporter iPS cells were dissociated into single cells in a manner similar to Example 2. Subsequently, the iPS cells were suspended in a DMEM/F12 medium containing Glutamax, 2% FBS, and PenStrep, and a combination of 10 micromolar Y-27632, 3 micromolar CHIR99021, and 1 micromolar TTNPB was added thereto. Subsequently, the cell suspension was transferred to a dish coated with 0.1% gelatin, and culture was conducted for 2 days. Thereafter, the medium was removed, the culture product was washed in PBS, and the iPS cells were then cultured for an additional 3 days (novel induction method 3) in a medium prepared by adding 1 micromolar TTNPB to a DMEM/F12 medium containing 2-mercaptoethanol, Glutamax, 10% KOCKOUT SR, 0.1 mM MEM NEAA, and PenStrep. After isolating GFP positive cells from obtained cells with flow cytometer, $1 \times 10^4$ GFP positive cells were mixed with $1 \times 10^5$ mouse metanephric cells obtained from E11.5 mouse embryo on a low cell adhesion plate (PrimeSurface). The next day, cell sphere was transferred on the Isopore™ Membrane Filters (Merck Millipore) floated on Improve MEM medium containing 10 micromolar Y-27632, 10% FBS and PenStrep. During culture, the medium was exchanged with fresh medium once every 3 days. Obtained cells were analyzed with immunostaining at 7 days after floating culture (FIG. 9). It was confirmed that luminal structure could be constructed with renal tubule cells differentiated from the OSR1 positive cells by mixed culture with organ.

INDUSTRIAL APPLICABILITY

According to the present invention, an intermediate mesoderm cell can be prepared from a pluripotent stem cell, such as an ES or iPS cell, without the use of a growth factor. The intermediate mesoderm cell is very useful for induction of differentiation into a cell that can be used in the field of regenerative medicine aimed at treatment of renal disorders.

All publications, patents, and patent applications cited herein are incorporated herein by reference in their entirety.

The invention claimed is:

1. A method for producing an intermediate mesoderm cell from a human pluripotent stem cell, the method comprising:
   (i) culturing the human pluripotent stem cell in a medium comprising a GSK-3 beta inhibitor, or a GSK-3 beta inhibitor and at least one of AM580 and TTNPB; and
   (ii) culturing the cell cultured in the culturing (i) in a medium comprising at least one of AM580 and TTNPB to produce the intermediate mesoderm cell.

2. The method of claim 1, wherein the GSK-3 beta inhibitor is CHIR99021.

3. The method of claim 2, wherein the medium in the culturing (i) comprises the GSK-3 beta inhibitor and one of AM580 and TTNPB, and the medium in the culturing (ii) comprises one of AM580 and TTNPB.

4. The method of claim 1, wherein the medium in the culturing (i) comprises the GSK-3 beta inhibitor and one of AM580 and TTNPB, and the medium in the culturing (ii) comprises one of AM580 and TTNPB.

5. The method of claim 1, wherein the medium in the culturing (i) comprises the GSK-3 beta inhibitor and at least one of AM580 and TTNPB.

6. The method of claim 1, wherein the human pluripotent stem cell is a human iPS cell or a human ES cell.

7. The method of claim 1, wherein a culture period of the culturing (i) is up to 2 days and a culture period of the culturing (ii) is at least 3 days.

8. The method of claim 7, wherein the culture period of the culturing (i) is 2 days and the culture period of the culturing (ii) is 8 days.

9. The method of claim 1, wherein a composition of the medium in the culturing (i) is different from a composition of the medium in the culturing (ii).

10. The method of claim 1, wherein the culturing (ii) further comprises assaying the cell cultured in the culturing (ii) for OSR1 such that an OSR1-positive cell is selected as the intermediate mesoderm cell.

11. A method for producing luminal structure constructed with renal tubule cells, the method comprising:
producing an intermediate mesoderm cell by the method of claim 1; and
forming renal tubule cells by suspension culturing the intermediate mesoderm cell such that a sphere consisting of the intermediate mesoderm cell is formed.

12. A method for producing luminal structure constructed with renal tubule cells, the method comprising:
producing an intermediate mesoderm cell by the method of claim 1; and
forming renal tubule cells by culturing the intermediate mesoderm cell with a metanephric cell obtained from a mouse embryo.

13. The method of claim 12, wherein the metanephric cell is obtained from an E11.5 mouse embryo.

14. A method for producing a plurality of intermediate mesoderm cells from a plurality of human pluripotent stem cells, the method comprising:
(i) dissociating the plurality of human pluripotent stem cells into single cells and culturing the dissociated human pluripotent stem cells in a medium comprising a GSK-3 beta inhibitor, or a GSK-3 beta inhibitor and at least one of AM580 and TTNPB; and
(ii) culturing the cells cultured in the culturing (i) in a medium comprising at least one of AM580 and TTNPB to produce the plurality of intermediate mesoderm cells.

15. The method of claim 14, wherein the medium in the culturing (i) further comprises a ROCK inhibitor.

16. The method of claim 15, wherein the ROCK inhibitor is Y-27632.

17. The method of claim 15, wherein the medium in the culturing (i) comprises the GSK-3 beta inhibitor, at least one of AM580 and TTNPB, and the ROCK inhibitor.

18. A method for producing a metanephric cell, the method comprising:
inducing differentiation of a human pluripotent stem cell into an intermediate mesoderm cell by (i) culturing the human pluripotent stem cell in a medium comprising a GSK-3 beta inhibitor, or a GSK-3 beta inhibitor and at least one of AM580 and TTNPB, and (ii) culturing the cell cultured in the culturing (i) in a medium comprising at least one of AM580 and TTNPB; and
inducing differentiation of the intermediate mesoderm cell by adhesion culturing the intermediate mesoderm cell to produce the metanephric cell.

19. The method of claim 18, wherein the metanephric cell comprises at least one selected from the group consisting of a metanephric mesenchyme cell, a metanephric stroma cell, an ureteric bud cell, podocyte, and a proximal tubule cell.

20. The method of claim 18,
wherein the adhesion culturing of the intermediate mesoderm cell occurs in a medium comprising at least one of Wnt3a and BMP7.

\* \* \* \* \*